US011752332B2

(12) United States Patent
Gimelli et al.

(10) Patent No.: US 11,752,332 B2
(45) Date of Patent: Sep. 12, 2023

(54) DEVICE THAT CAN BE HELD IN ONE HAND FOR ELECTRICALLY ASSISTED SKIN TREATMENT, ADDITIONAL PART FOR SAID DEVICE AND BLISTER PACK FOR SAID ADDITIONAL PART

(71) Applicant: Swiss Spa System Ltd., Hong Kong (CN)

(72) Inventors: Bruno Gimelli, Zollikofen (CH); James N. Doyle, Westlake, OH (US)

(73) Assignee: Swiss Spa System Ltd., Hong Kong (CN)

( * ) Notice: Subject to any disclaimer, the term of this patent is extended or adjusted under 35 U.S.C. 154(b) by 0 days.

(21) Appl. No.: 17/950,320

(22) Filed: Sep. 22, 2022

(65) Prior Publication Data

US 2023/0025257 A1    Jan. 26, 2023

Related U.S. Application Data

(62) Division of application No. 16/755,524, filed as application No. PCT/EP2018/077796 on Oct. 11, 2018, now Pat. No. 11,484,707.

(30) Foreign Application Priority Data

Oct. 12, 2017   (DE) .................... 10 2017 123 809.3

(51) Int. Cl.
*A61N 1/30*   (2006.01)
*A61N 1/04*   (2006.01)
*A61N 1/32*   (2006.01)

(52) U.S. Cl.
CPC .......... *A61N 1/303* (2013.01); *A61N 1/0448* (2013.01); *A61N 1/328* (2013.01)

(58) Field of Classification Search
CPC ...... A61N 1/303; A61N 1/0448; A61N 1/328; A61N 1/0428; A61N 1/30; A61M 37/00; A61M 2037/0007
See application file for complete search history.

(56) References Cited

U.S. PATENT DOCUMENTS

| 6,119,038 A | 9/2000 | Cook ................. A61N 1/328 604/20 |
| 6,477,410 B1 | 11/2002 | Henley .............. A61N 1/30 604/20 |

(Continued)

FOREIGN PATENT DOCUMENTS

| DE | 1 805 711 U | 2/1980 |
| DE | 90 17 597 U1 | 5/1991 |

(Continued)

OTHER PUBLICATIONS

German Search Report issued in German application No. 10 2017 123 809.3 dated Jul. 4, 2018 (Nine (9) pages).

(Continued)

*Primary Examiner* — Mallika D Fairchild
(74) *Attorney, Agent, or Firm* — Crowell & Moring LLP

(57) ABSTRACT

An additional part for a hand-held device for electrically assisted skin treatment includes a ring which is clippable onto the hand-held device. The additional part further includes an absorbent carrier material where the absorbent carrier material is soaked with an active ingredient and where the absorbent carrier material is fastened to the ring.

5 Claims, 3 Drawing Sheets

(56) References Cited

U.S. PATENT DOCUMENTS

| | | | |
|---|---|---|---|
| 6,499,595 B1 | 12/2002 | Petricca | ............... B65D 1/26 |
| | | | 53/412 |
| 2003/0199808 A1 | 10/2003 | Henley | ............... A61N 1/30 |
| | | | 604/20 |
| 2004/0049147 A1 | 3/2004 | Edel | ............... A61N 1/325 |
| | | | 604/20 |
| 2008/0262414 A1* | 10/2008 | Barsness | ............ A61N 1/0428 |
| | | | 604/20 |
| 2008/0262581 A1 | 10/2008 | Barsness | ............ A61N 1/044 |
| | | | 607/115 |
| 2009/0124985 A1 | 5/2009 | Hasenoehrl | ........... A61Q 19/00 |
| | | | 604/289 |
| 2009/0198159 A1 | 8/2009 | Linzell | ............... B65D 83/08 |
| | | | 601/138 |
| 2016/0022010 A1 | 1/2016 | Rabe | ............... A45D 34/04 |
| | | | 132/320 |
| 2016/0310727 A1 | 10/2016 | Planard-Luong | |

FOREIGN PATENT DOCUMENTS

| | | | |
|---|---|---|---|
| DE | 10 2012 009 514 A1 | 11/2013 | |
| WO | WO 9006153 A1 | 6/1990 | ............ A61N 1/30 |
| WO | WO 00/30711 A1 | 6/2000 | |
| WO | WO 03/018116 A2 | 3/2003 | |
| WO | WO 2005/087308 A1 | 9/2005 | |

OTHER PUBLICATIONS

PCT/EP2018/077796, International Search Report dated Feb. 1, 2019 (Two (2) pages).

* cited by examiner

DEVICE THAT CAN BE HELD IN ONE HAND FOR ELECTRICALLY ASSISTED SKIN TREATMENT, ADDITIONAL PART FOR SAID DEVICE AND BLISTER PACK FOR SAID ADDITIONAL PART

CROSS REFERENCE TO RELATED APPLICATIONS

This application is a division of patent application Ser. No. 16/755,524, filed Apr. 10, 2020, which is the National Stage of PCT International Application No. PCT/EP2018/077796, filed Oct. 11, 2018, which claims priority under 35 U.S.C. § 119 from German Patent Document No. 10 2017 123 809.3, filed Oct. 12, 2017, the entire disclosures of which are herein expressly incorporated by reference.

BACKGROUND AND SUMMARY OF THE INVENTION

The invention relates to a hand-held device for electrically assisted skin treatment, comprising:
  a skin electrode, which is placeable on the skin region to be treated,
  a hand electrode, which is on the outer side of the device and in contact with the hand when the device is held in the hand by the user during use,
  an electrical power source in the device, the terminals of which are electrically connected to the electrodes during operation of the device.

By way of example, such a device in described in WO 2005/087308 A1 or in WO 00/30711. While, according to the older application WO 00/30711 A1, the skin electrode is still integral with a base part, WO 2005/087308 A1 proposes that the skin electrode be designed in the form of an interchangeable cap, with differently shaped caps being provided for the treatment of specific skin regions. The devices according to the two documents provide for the influence of active ingredients in a skin cream to be enhanced by virtue of a current with negative or positive polarity being guided into the body via the skin electrode. The active ingredients can be both cosmetically and medically active ingredients, e.g. for a wound healing treatment. The active ingredients of the cream are guided into the skin in the case of one polarity while dirt migrates from the skin into a cleansing cream during the other polarity. In both cases, an appropriate cream must first be applied before the device is used.

To the extent that this relates to the mechanical and electrical design of the device, the content of both documents is incorporated in the content of the present application.

Correct metering is problematic in this case. Not enough active ingredient is introduced into the skin or not enough dirt is removed in the case of a dose that is too low, and a dose that is too high cannot be fully exploited, and so the cream must be removed again, partly unused, following the skin treatment. Moreover, the hands must initially be cleaned following the application of the cream onto the skin so that the skin treatment device can be securely held.

DE 1 805 711 U1 and DE 90 17 597 U1 have already proposed the placement of a sponge soaked with an active ingredient in front of the electrode. To this end, an inwardly bent collar extends around a plate-shaped electrode, the collar receiving a sponge soaked with an active ingredient. However, this also has the problem of the sponge initially having to be soaked and subsequently having to be placed on the electrode, with the hands being wetted with the active ingredient which must initially be washed away so that the device can subsequently be held securely.

The invention is consequently based on the object of simplifying the application of a cream.

To this end, the invention provides for an absorbent carrier material, soaked with an active ingredient, to be located in front of the skin electrode and for the carrier material to be fastened to a ring that can be clipped onto the device, wherein the carrier material extends over the skin electrode when the ring is in a clipped-on state.

A ring with a carrier material soaked with an active ingredient, the carrier material being soaked with an active ingredient in a precisely metered amount, is provided for the user in a suitable way. The user can take the ring and clip it on the device without their hands being wetted by a cream or the active ingredient contained therein. Consequently, the cream with the active ingredient is brought in front of the head of the cap, and so the skin treatment can be started immediately thereafter.

An embodiment of the carrier material provides for it to consist of a strip having two ends and an intermediate section situated therebetween, the ends of the strip being fastened to the ring and the intermediate section of the strip extending over the skin electrode when the ring is in a clipped-on state.

Preferably, the ring is matched to the contour of the device such that the clipped-on ring surrounds the device with as little play as possible. Furthermore, the head of the device tapers upward such that the ring can be placed onto the device over the head until the ring reaches a region of the device which, in terms of its outer contour, corresponds to the inner contour of the ring.

Since pulling forces on the carrier material arise when the device is moved over the skin, it is necessary to secure the ring against being pulled off. Therefore, the invention further provides for the ring to have at least one inwardly directed latching lug, which engages behind a holding edge on the device.

In an embodiment in which:
  the skin electrode has the form of a cap connected to a base, wherein the cap has a foot region near the base and a head region that is placeable on the skin to be treated,
  the hand electrode is formed on the outer side of the base which is in contact with the hand when the device is held in the hand by the user during use, and
  the electrical power source is disposed in the base,
  the invention provides for:
  the carrier material to extend over the head of the cap when the ring is in a clipped-on state.

The ring surrounds the foot region of the cap as tightly as possible so that the lower edge of the cap forms the holding edge for one or more inwardly directed latching lugs on the ring.

In an embodiment in which the cap is clipped onto a shoulder on the base, there is a gap between the lower edge of the cap and a step on the base, the latching lug engaging in the gap.

Since this gap should be neither very deep nor very wide, the latching lug must not project a great distance beyond the inner lateral surface of the ring. In order nevertheless to provide the latching lug with good flexibility, provision is made for the ring to have a transverse groove on its inner side, the latching lug being formed on the bottom of the groove.

Preferably, at least two latching lugs are provided, which are located opposite one another on the ring.

The carrier material preferably has the form of a strip and the skin electrode has an elongate head with a half-cylindrical upper end, the strip extending thereover.

For this purpose, the ring has the form of an oval with two longitudinal sections, which are interconnected by way of arches, wherein the strip is fastened to the longitudinal sections. The two arches serve as grips that can be used to grasp the ring without the fingers coming into contact with the carrier material.

The carrier material can consist of very different materials. An absorbent fabric, a sponge or a felt would be conceivable.

The invention is furthermore advantageous in that the ring can be formed as an additional part, which can also be used on devices that are already commercially available.

Accordingly, the additional part consists of a ring which can be clipped onto a skin treatment device, an absorbent carrier material, soaked with an active ingredient, being fastened to the ring. As already explained, this ring has an oval shape with two longitudinal sections, which are interconnected by way of arches, wherein the carrier material consists of a strip, which extends from one longitudinal section to the other longitudinal section. The ring in each case has at least one latching lug on the inner side of the longitudinal sections, the latching lug protruding over the inner lateral surface of the ring. In order to ensure a sufficient bendability of the latching lugs, provision is made for the latching lugs to be arranged in transverse grooves on the ring.

To prevent the active ingredient from evaporating or oxidizing prior to use, the additional part is stored in vacuum-tight fashion in hermetically sealed packaging, which is only opened when required. Such packaging allows the use of a cream with active ingredients but without preservatives.

So-called blister packs are a form of the packaging. The additional parts are made available in such blister packs, wherein the blister pack consists of a shell with a film cover. Located in the shell is a circumferential depression for containing the ring, wherein the ring is placed into the depression in such a way that the strip faces the bottom of the shell and the central part of the strip extends in an arch through the ring.

The invention should be explained in more detail below on the basis of an exemplary embodiment.

DETAILED DESCRIPTION OF THE DRAWINGS

Figure 1:
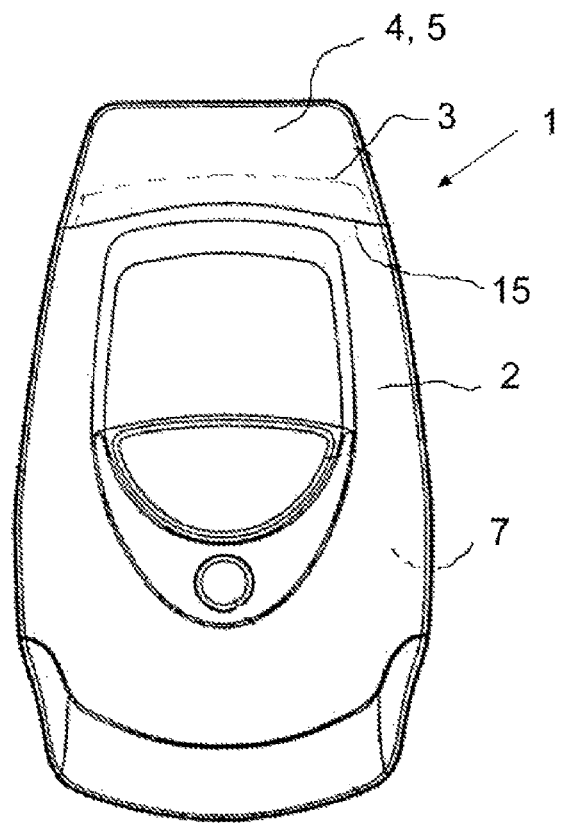
FIG. 1 shows a typical skin treatment device, in which the invention is used.

Reference is initially made to FIG. 1.

FIG. 1 shows a typical skin treatment device 1 with a base 2, which can be held in the hand, wherein the base 2 has on its upper end a shoulder 3 (illustrated in dash—dotted fashion since it is concealed), onto which a skin electrode 4 in the form of a cap 5 can be clipped and secured by means of a clip not shown here. However, the invention is not only applicable to skin treatment devices with an interchangeable cap 5 but also to devices where the cap is designed in one piece and integral with the base 2.

A hand electrode 7 which is in contact with the hand when the base 2 is gripped is located on the back side of the base 2 not visible here. Furthermore, situated in the base 2 there is a power source in the form of, e.g., batteries or rechargeable batteries, the terminals of which can be brought into contact with the two electrodes 4, 7 such that, when the skin electrode 4 is placed on the skin, a closed circuit via the body of the person is established. The cap 5 has an elongate form, which tapers from the foot region to the head, wherein the head typically merges into a half-cylindrical edge that can be guided over the skin.

Slight bulges of the edge or a cap in the form of a comb are also conceivable, with the ends of the prongs, however, likewise being enveloped by a half cylinder.

Figure 2:
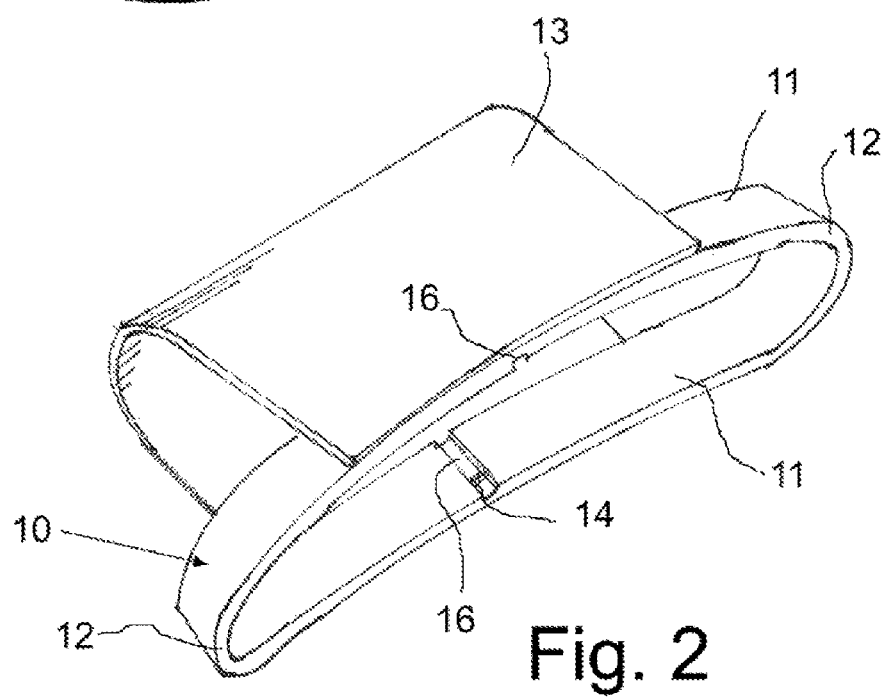
FIG. 2 shows a perspective view of a ring with a carrier material fastened thereto.

In order to make the cream with an active ingredient available, provision is made of a ring 10 as per FIG. 2. The latter has an oval shape with two longitudinal sections 11, which are interconnected by way of arches 12, wherein a strip 13 that serves as a carrier material for a cream extends from the outer side of one longitudinal section 11 to the outer side of the other longitudinal section 11.

The inner contour of the ring 10 is matched to the foot region of the cap 5 such that the ring 10 can be placed there with a tight fit, the strip 13 extending over the head of the cap 5. The carrier material can be a strip 13 made of a sponge, a fabric or a felt.

Figure 6:
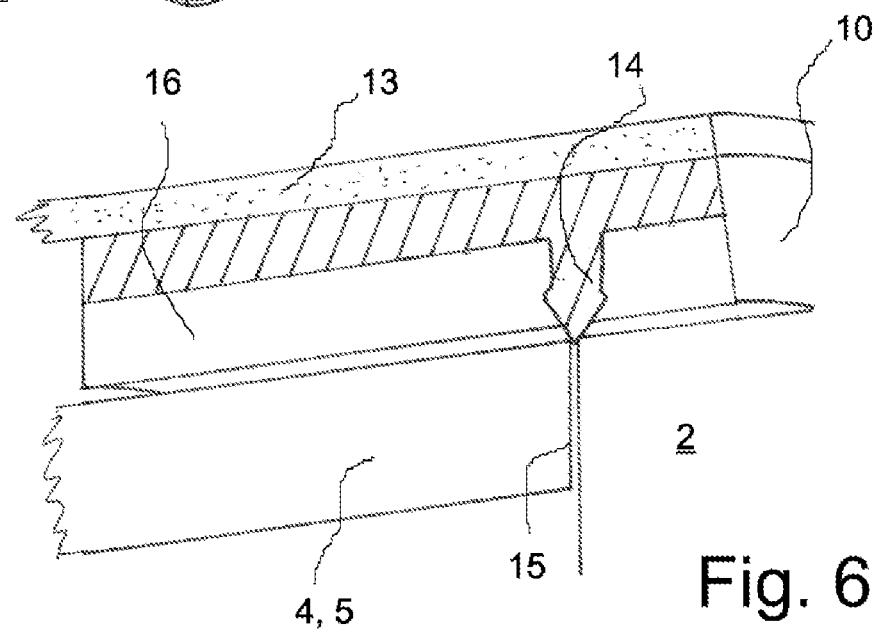
FIG. 6 shows a partial cross section through the device with a clipped-on ring, wherein a latching lug on the ring engages in a gap on the device.

To secure the ring 10, small latching lugs 14 are provided in each case on the inner side of the ring, in the center of the longitudinal section 11, the latching lugs ending in a sharp edge and thus engaging in a gap 15 between the base 2 and the edge of the cap 5, as shown in FIG. 6.

However, the latching lugs can also engage behind holding edges on separately formed pockets in the device.

In order to ensure sufficient mobility of the latching lugs 14, however, these are let into the bottom of a respective transverse groove 16 in the inner side of the longitudinal section 11 of the ring 10, with their tip slightly protruding beyond the edge of the groove.

The rings 10 with the soaked strip 13 form additional parts which can be purchased separately from the device, packaged in so-called blister packs 20.

Figure 3:
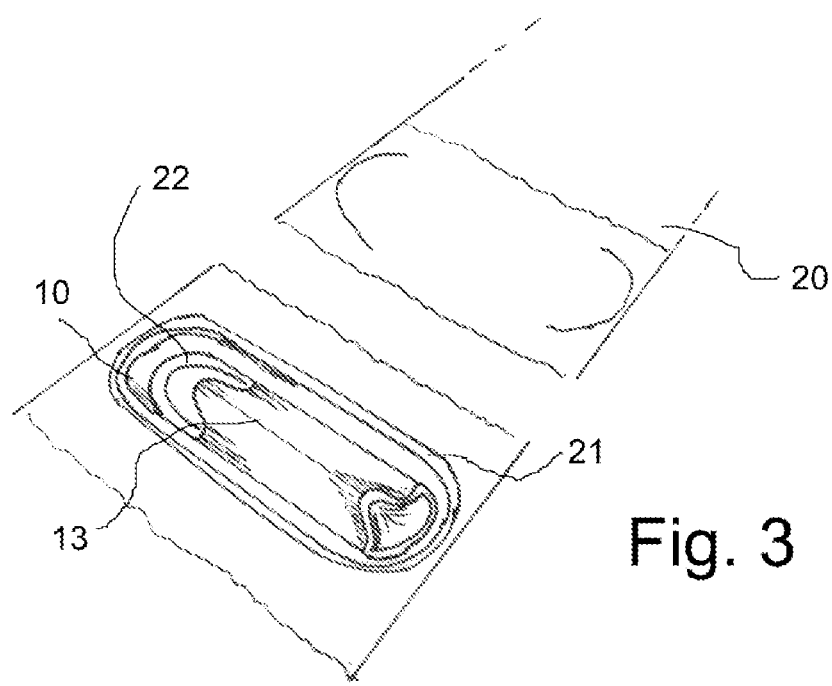
FIG. 3 shows a blister pack with inserted rings.
Figure 4:
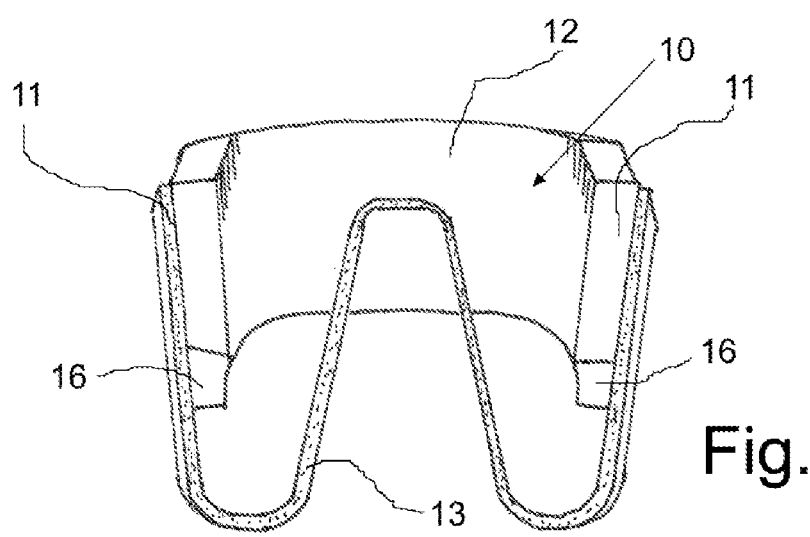
FIG. 4 shows a cross section through the ring, in which the carrier material fastened to the ring is folded for insertion into the blister pack.

As shown in FIG. 3, a blister pack 20 consists of a shell 21 with a circumferential depression 22, in which the ring 10 is inserted, wherein, in accordance with FIG. 4, which shows a cross section through the ring 10, the strip 13, proceeding from the longitudinal sections 11 of the ring 10, is initially directed downward in the direction of the bottom of the circumferential depression 22 and then extends in an arch through the inner region of the ring 10. This obtains a compact grouping which keeps the blister pack volume low.

The shell 21 is typically sealed by an opaque or transparent film, not shown here.

Before the ring 10 is inserted into the blister pack, the former is soaked with a cream that contains an active ingredient. Sealing the shell 21 with a film prevents the carrier material from drying up.

Figure 5:
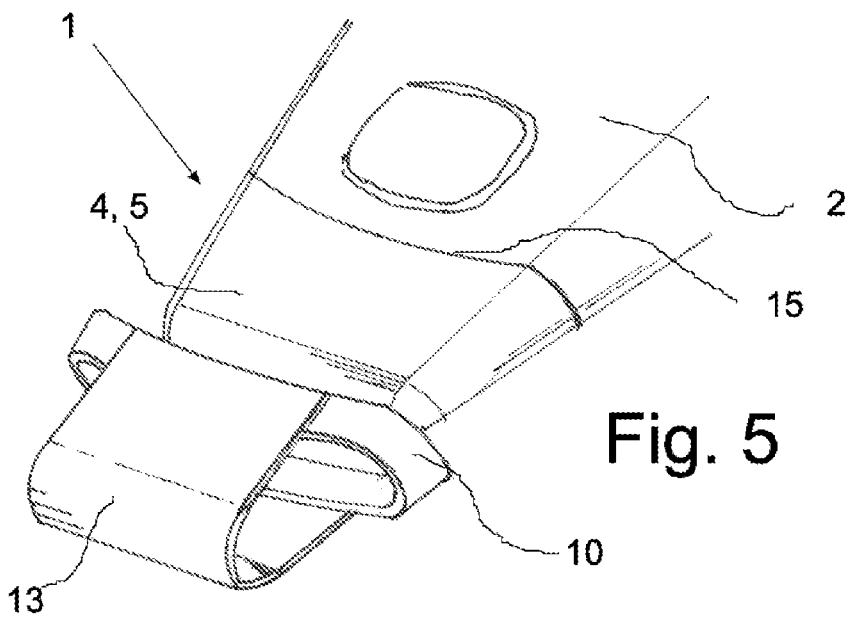
FIG. 5 shows a ring that is being clipped onto the device.

For use, the film is removed, the ring 10 is gripped by its arches 12 and—as shown in FIG. 5—clipped onto the cap 5 until the latching lugs 14 clip into the gap 15 between the cap 5 and the base 2 as per FIG. 6. This ensures a sufficient hold of the ring 10 on the device so that the head of the cap, over which the strip is stretched, can be guided over the skin without the ring 10 detaching from the device.

After the treatment, the ring 10 can be gripped by the arches 12 again, can be pulled off the cap and can be subsequently disposed of.

The rings 10 can be designed in different colors for the purpose of indicating the type of active ingredients of the cream in the carrier material.

| List of reference characters | |
|---|---|
| 1 | Skin treatment device |
| 2 | Base |
| 3 | Shoulder |
| 4 | Skin electrode |
| 5 | Cap |
| 7 | Hand electrode |
| 10 | Ring |
| 11 | Longitudinal sections |
| 12 | Arches |
| 13 | Strip |
| 14 | Latching lugs |
| 15 | Gap |
| 16 | Transverse groove |
| 20 | Blister pack |
| 21 | Shell |
| 22 | Depression |

What is claimed is:

1. An additional part for a hand-held device for electrically assisted skin treatment, comprising:
    a ring which is clippable onto the hand-held device; and
    an absorbent carrier material, wherein the absorbent carrier material is soaked with an active ingredient and wherein the absorbent carrier material is fastened to the ring;
    wherein the ring has an oval shape with a first and a second longitudinal section which are interconnected by an arch and wherein the absorbent carrier material consists of a strip which extends from the first longitudinal section to the second longitudinal section.

2. The additional part according to claim 1, wherein the ring has a latching lug on an inner side and wherein the latching lug protrudes over an inner lateral surface of the ring.

3. The additional part according to claim 2, wherein the latching lug is disposed in a transverse groove on the ring.

4. The additional part according to claim 1, wherein the additional part is stored in hermetically sealed packaging.

5. A blister pack, comprising:
    the additional part according to claim 1; and
    a shell with a film cover, wherein a circumferential depression for containing the ring is located in the shell and wherein the strip faces a bottom of the shell and a central part of the strip extends in an arch through the ring.

* * * * *